United States Patent
Hallinan et al.

(10) Patent No.: US 7,790,919 B2
(45) Date of Patent: *Sep. 7, 2010

(54) REMOVING HYDROCARBON IMPURITIES FROM ACETIC ACID PRODUCTION PROCESS

(75) Inventors: Noel C. Hallinan, Loveland, OH (US); Brian A. Salisbury, Oxford, PA (US)

(73) Assignee: Lyondell Chemical Technology, L.P., Wilmington, DE (US)

( * ) Notice: Subject to any disclaimer, the term of this patent is extended or adjusted under 35 U.S.C. 154(b) by 255 days.

This patent is subject to a terminal disclaimer.

(21) Appl. No.: 12/077,098

(22) Filed: Mar. 17, 2008

(65) Prior Publication Data

US 2009/0229966 A1   Sep. 17, 2009

(51) Int. Cl.
*C07C 51/12* (2006.01)
(52) U.S. Cl. .................................................. 562/519
(58) Field of Classification Search .................. 562/519
See application file for complete search history.

(56) References Cited

U.S. PATENT DOCUMENTS

| | | | |
|---|---|---|---|
| 4,102,922 A | 7/1978 | Price | |
| 5,817,869 A | 10/1998 | Hinnenkamp et al. | |
| 5,932,764 A | 8/1999 | Morris et al. | |
| 6,552,221 B1 * | 4/2003 | Hallinan et al. | 562/519 |
| 6,667,418 B2 * | 12/2003 | Broussard et al. | 562/519 |

OTHER PUBLICATIONS

U.S. Appl. No. 12/383,896, filed Mar. 2009, Hallinan et al.*

\* cited by examiner

*Primary Examiner*—Taylor Victor Oh
(74) *Attorney, Agent, or Firm*—Shao-Hua Guo

(57) ABSTRACT

A method for removing hydrocarbon impurities from an acetic acid production process is disclosed. The method comprises distilling at least a portion of the heavy organic phase from the decanter of the acetic acid production process into a vapor stream comprising the majority of methyl iodide (i.e., over 50% of the methyl iodide from the heavy organic phase) and a bottoms stream comprising the majority of acetic acid, methyl acetate, methyl iodide and the hydrocarbon impurity (i.e., over 50% of each of the components from the heavy organic phase); extracting the bottoms stream with water, an acetic acid aqueous solution, or with a methanol aqueous solution to form an organic phase comprising the majority of the hydrocarbon impurity (over 50% of the hydrocarbon impurity from the bottom stream) and an aqueous phase comprising the majority of methyl iodide (over 50% of the methyl iodide from the bottoms stream); and recycling the aqueous phase to the carbonylation reaction.

15 Claims, No Drawings

REMOVING HYDROCARBON IMPURITIES FROM ACETIC ACID PRODUCTION PROCESS

FIELD OF THE INVENTION

The invention relates to the preparation of acetic acid. More particularly, the invention relates to a method for removing hydrocarbon impurities from the acetic acid production process.

BACKGROUND OF THE INVENTION

The carbonylation of methanol produces acetic acid:

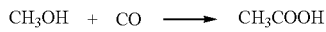

Prior to 1970, acetic acid was made using a cobalt catalyst. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One problem associated with the original Monsanto process is that a large amount of water (about 14%) is needed to produce hydrogen in the reactor via the water-gas shift reaction

Water and hydrogen are needed to react with precipitated Rh(III) and inactive [Rh$_4$(CO)$_2$] to regenerate the active Rh(I) catalyst. This large amount of water increases the amount of hydrogen iodide, which is highly corrosive and leads to engineering problems. Further, removing a large amount of water from the acetic acid product is costly.

In the late '70s Celanese modified the carbonylation process by adding lithium iodide salt to the carbonylation. Lithium iodide salt increases the catalyst stability by minimizing the side reactions that produce inactive Rh(III) species and therefore the amount of water needed is reduced. However, the high concentration of lithium iodide salt promotes stress crack corrosion of the reactor vessels. Furthermore, the use of iodide salts increases the iodide impurities in the acetic acid product.

In the early '90s, Millennium Petrochemicals developed a new rhodium carbonylation catalyst system that does not use iodide salt. The catalyst system uses a pentavalent Group VA oxide such as triphenylphosphine oxide as a catalyst stabilizer. The Millennium catalyst system not only reduces the amount of water needed but also increases the carbonylation rate and acetic acid yield. See U.S. Pat. No. 5,817,869.

One challenge still facing the industry is that lowering water concentration in the methanol carbonylation increases the formation of hydrocarbon impurities such as alkanes and aromatics. Methods for removing alkanes from acetic acid are known. For instance, U.S. Pat. No. 4,102,922 discloses an alkane removal method. According to the '922 patent, a slip stream from the heavy phase which comprises methyl iodide, acetic acid, water and alkanes is fed to an alkane distillation column with an overhead temperature of about 75° C. and a bottoms temperature of about 142° C. The bottoms temperature is run significantly higher than the overhead in order to minimize methyl iodide loss to the bottoms stream. The overhead of the alkane distillation, comprising mainly methyl iodide, is recycled to the reaction section. The bottoms stream comprising about 50% acetic acid and about 40% alkanes is removed from the system as waste. One problem associated with this method is that due to the high bottoms temperature, low boiling alkanes such as 2-methylpentane come with the overhead methyl iodide. This results in a build up of the low boiling alkanes in the reaction system as the overhead methyl iodide is recycled into the carbonylation reaction.

A new method for removing alkanes and other hydrocarbon impurities from the acetic acid production process is needed. Ideally, the method can effectively remove both high boiling and low boiling hydrocarbon impurities from the acetic acid production process.

SUMMARY OF THE INVENTION

The invention is a method for removing hydrocarbon impurities from the acetic acid production process. The method comprises reacting methanol and carbon monoxide in the presence of a carbonylation catalyst, a catalyst stabilizer, methyl iodide, water and methyl acetate to produce an acetic acid stream containing a hydrocarbon impurity. At least a portion of the acetic acid stream is flashed into a vapor stream comprising acetic acid, water, methanol, methyl acetate, methyl iodide and the hydrocarbon impurity, and a liquid stream comprising the catalyst and the catalyst stabilizer. The vapor stream is separated by distillation into a product stream comprising acetic acid and a minor amount of water and heavy impurities such as propionic acid, and an overhead stream comprising methyl iodide, water, methyl acetate, acetic acid and the hydrocarbon impurity. The overhead stream is condensed and separated into a light, aqueous phase comprising water, acetic acid, and methyl acetate, and a heavy, organic phase comprising methyl iodide, acetic acid, methyl acetate, and the hydrocarbon impurity. At least a portion of the heavy, organic phase is distilled to form a vapor stream comprising the majority of methyl iodide (over 50% of the methyl iodide from the heavy organic phase) and a bottoms stream comprising the majority of acetic acid, methyl acetate, methyl iodide, and the hydrocarbon impurity (over 50% of each component from the heavy organic phase). The bottom stream is extracted with water, or an acetic acid aqueous solution, or with a methanol aqueous solution to form an organic phase comprising the majority of the hydrocarbon impurity (over 50% of the hydrocarbon impurity from the bottoms stream) and an aqueous phase comprising the majority of methyl iodide (over 50% of the methyl iodide from the bottoms stream). The aqueous phase is recycled to the carbonylation reactor.

DETAILED DESCRIPTION OF THE INVENTION

Hydrocarbon impurities are produced by the side reactions of methanol carbonylation. Examples of hydrocarbon impurities include alkanes, alkenes, and aromatics. Alkane impurities commonly seen in the methanol carbonylation are C3-C12 alkanes including propane, butane, pentane, 2-methylbutane, 2,3-dimethylbutane, 2-methyl pentane, 3-methylpentane, hexane, octane, decane, cyclohexane, the like, and mixtures thereof. Commonly seen alkenes include propylene, butene, octene, the like, and mixtures thereof. Commonly seen aromatics include benzene, n-propylbenzene, toluene, xylene, the like, and mixtures thereof.

The carbonylation reaction is performed in the presence of a carbonylation catalyst and a catalyst stabilizer. Suitable carbonylation catalysts include those known in the acetic acid industry. Examples of suitable carbonylation catalysts include rhodium catalysts and iridium catalysts.

Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]H^+$, $Ir_4(CO)_{12}$, $IrCl_3.4H_2O$, $IrBr_3.4H_2O$, $Ir_3(CO)_{12}$, $Ir_2O_3$, $IrO_2$, $Ir(acac)(CO)_2$, $Ir(acac)_3$, $Ir(OAc)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are acetates.

Preferably, the reaction is performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817, 869. Phosphine oxides are more preferred. Triphenylphosphine oxides are most preferred.

The carbonylation reaction is preferably performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The reaction is preferably performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %. Alternatively, methyl acetate or a mixture of methyl acetate and methanol from byproduct streams of the hydroysis/methanolysis of polyvinyl acetate can be used for the carbonylation reaction.

The reaction is performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Hydrogen may also be fed into the reactor. Addition of hydrogen can enhance the carbonylation efficiency. Preferably, the concentration of hydrogen is from about 0.1 mol % to about 5 mol % of carbon monoxide in the reactor. More preferably, the concentration of hydrogen is from about 0.3 mol % to about 3 mol % of carbon monoxide in the reactor.

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by the hydrogen iodide present in the reactor and then reacts with carbon monoxide and water to give acetic acid and regenerate hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

An acetic acid product stream is withdrawn from the reactor and is separated, by a flash separation, into a liquid fraction comprising the catalyst and the catalyst stabilizer and a vapor fraction comprising the acetic acid product, the reactants, water, methyl iodide, and impurities generated during the carbonylation reaction including alkanes, alkenes, and aromatics. The liquid fraction is recycled to the carbonylation reactor. The vapor fraction is then passed to a distillation column.

The distillation column, the so-called "light ends distillation," separates an overhead comprising methyl iodide, water, methanol, methyl acetate, and the hydrocarbon impurities from an acetic acid stream comprising acetic acid, a small amount of water, and some heavy impurities such as propionic acid. The acetic acid stream may be passed to a drying column to remove water and then be subjected to distillation, the so-called "heavy ends distillation," to remove the heavy impurities.

The overhead stream from the light ends distillation usually comprises from about 60 wt % to about 90 wt % of methyl iodide, from about 5 wt % to about 15 wt % of methyl acetate, from about 1 wt % to about 10 wt % of acetic acid, 1 wt % or less of water, from about 1 wt % to about 10 wt % of hydrocarbon impurities, and about 2 wt % or less of aldehyde impurities based on the total weight of the overhead.

The overhead stream is condensed and separated in a decanter to a light, aqueous phase and a heavy, organic phase. The heavy, organic phase comprises predominantly methyl iodide (greater than 50%) and the hydrocarbon impurities. The light, aqueous phase comprises predominantly water (greater than 50%), acetic acid, and methyl acetate. The aqueous phase is usually recycled to the reactor or to the light ends distillation.

At least a portion of the heavy, organic phase is distilled to form a vapor stream comprising the majority of methyl iodide (over 50% of the methyl iodide from the heavy organic phase) and a bottoms stream comprising the majority of acetic acid, methyl acetate, methyl iodide, and the hydrocarbon impurities (over 50% of each component from the heavy organic phase). The overhead temperature of the distillation is preferably below about 75° C. so that there is no significant amount of hydrocarbon impurities coming out with the vapor stream. More preferably, the overhead temperature of the distillation is within the range of about 43° C. (boiling point of methyl iodide) to about 75° C. Most preferably, the overhead temperature of the distillation is within the range of about 43° C. to about 60° C. The particularly preferred overhead temperature of the distillation is within the range of about 43° C. to about 45° C. The closer the overhead temperature of the distillation to the boiling point of methyl iodide, the less the amount of hydrocarbon impurities existing in the vapor stream. The vapor stream is recycled to the carbonylation reaction. Lowering the overhead temperature of the heavy phase distillation, although reducing the hydrocarbon impurities in the vapor stream, results in a higher concentration of methyl iodide in the bottoms stream. According to current industrial practice, the bottoms stream is disposed as a waste. Thus, an increased amount of methyl iodide, an expensive material, is wasted. The method of the invention comprises an extracting step to remove methyl iodide from the bottom stream and recycling it to the carbonylation reaction.

The bottoms stream is extracted with water, a methanol aqueous solution, or with an acetic acid aqueous solution to form an organic phase comprising the majority of the hydrocarbon impurities (over 50% of the hydrocarbon impurities from the bottoms stream) and an aqueous phase comprising the majority of water, acetic acid, and methyl iodide (over 50% of each component from the bottoms stream). The organic phase is optionally disposed of and the aqueous phase is recycled to the carbonylation reaction. Preferably, from about 5% to about 100% of the heavy, organic phase from the decanter is subjected to the distillation and extraction. More preferably, from about 5% to about 50% of the heavy, organic phase from the decanter is subjected to the distillation and extraction.

Water, methanol, and acetic acid are the carbonylation starting materials or product. Thus, using water, methanol aqueous solutions, or acetic acid aqueous solutions as the extracting solutions do not introduce any foreign substances into the carbonylation process. Water is essential to cause the phase separation during the extraction. Methyl iodide has low solubility in water in the absence of methanol or acetic acid. Thus, acetic acid aqueous solutions or methanol aqueous solutions are the preferred extracting solutions particularly when the bottoms stream of the alkanes distillation contains insufficient amount of acetic acid to aid the methyl iodide distribution in favor of the aqueous phase. The concentration of the acetic acid or methanol in the extracting solutions depends on the concentration of acetic acid in the bottoms stream of the alkanes distillation. Typically, the ratio of acetic acid/water or methanol/water is from 10/90 to 90/10 (V/V). Preferably, the ratio of acetic acid/water or methanol/water in the extracting solution is from 50/50 to 90/10. The extracting solution to the bottoms stream of the alkanes distillation is typically in the range of 75/25 to 25/75 (V/V). The bottoms stream of the alkanes distillation can be extracted more than once if desired.

The following examples are merely illustrative. Those skilled in the art will recognize many variations that are within the spirit of the invention and scope of the claims.

EXAMPLE 1-5

Extraction of Decane with Acetic Acid Aqueous Solution

A simulated alkane distillation bottoms stream (10 mL, containing 15 wt % of methyl iodide, 15 wt % of decane, and 70 wt % of acetic acid) is mixed with an acetic acid aqueous solution (10 mL) in a separation funnel at room temperature (25° C.). A phase separation occurs. The aqueous phase and the organic phase are analyzed by ATR (attenuated total reflectance) infrared probe measurements. The results are listed in Table 1.

TABLE 1

Extraction of Decane with Acetic Acid Aqueous Solution

| Ex. No. | AcOH/H$_2$O (V/V) Extracting Solution | Organic/ Aqueous (W/W) | Organic phase composition, wt % | | | Aqueous phase Composition, wt % | | | |
|---|---|---|---|---|---|---|---|---|---|
| | | | Decane | MeI | AcOH | Decane | MeI | AcOH | H$_2$O |
| 1 | 60/40 | 0.097 | 73.0 | 22.1 | 4.9 | 1.3 | 6.3 | 71.5 | 20.9 |
| 2 | 75/25 | 0.089 | 74.4 | 18.1 | 7.5 | 1.7 | 6.7 | 78.7 | 12.9 |
| 3 | 80/20 | 0.084 | 74.2 | 16.9 | 8.9 | 2.1 | 6.8 | 80.7 | 10.4 |
| 4 | 85/15 | 0.078 | 73.9 | 15.8 | 10.3 | 2.5 | 7.0 | 82.8 | 7.7 |
| 5 | 90/10 | 0.062 | 73.3 | 14.1 | 12.6 | 3.6 | 7.2 | 84.2 | 5.0 |

EXAMPLE 6-10

Extraction of Decane with Methanol Aqueous Solution

Examples 1-5 are repeated but the extracting solutions are methanol aqueous solutions instead of acetic acid solutions. The results are listed in Table 2.

TABLE 2

Extraction of Decane with Methanol Aqueous Solution

| Ex. No. | MeOH/H$_2$O (V/V) extracting solution | Organic/ aqueous (W/W) | Organic phase composition, wt % | | | Aqueous phase composition, wt % | | | | |
|---|---|---|---|---|---|---|---|---|---|---|
| | | | Decane | MeI | AcOH | Decane | MeOH | MeI | AcOH | H$_2$O |
| 6 | 60/40 | 0.090 | 77.8 | 20.9 | 1.3 | 1.4 | 27.0 | 7.0 | 42.0 | 22.6 |
| 7 | 75/25 | 0.083 | 81.9 | 16.6 | 1.5 | 1.7 | 34.1 | 7.7 | 42.3 | 14.2 |
| 8 | 80/20 | 0.077 | 83.0 | 15.6 | 1.4 | 2.2 | 36.3 | 7.8 | 42.3 | 11.4 |
| 9 | 85/15 | 0.069 | 85.0 | 13.4 | 1.6 | 2.8 | 38.5 | 8.1 | 42.1 | 8.5 |
| 10 | 90/10 | 0.063 | 85.9 | 12.4 | 1.7 | 3.3 | 40.7 | 8.2 | 42.1 | 5.7 |

EXAMPLE 11-13

Extraction of 2,2-Dimethylbutane with Methanol Aqueous Solution

Example 6 is repeated except 2,2-dimethylbutane (DMB), instead of decane, is used and the extracting solutions are water, 30/70, and 70/30 methanol/water solutions, respectively, in Examples 11, 12, and 13. The results are listed in Table 3.

TABLE 3

Extraction of DMB with Methanol Aqueous Solution

| Ex. No. | MeOH/H$_2$O (V/V) extracting solution | Organic/ aqueous (W/W) | Organic phase composition, wt % | | | Aqueous phase composition, wt % | | | | |
|---|---|---|---|---|---|---|---|---|---|---|
| | | | DMB | MeI | AcOH | DMB | MeOH | MeI | AcOH | H$_2$O |
| 11 | 0/100 | 0.110 | 55.9 | 41.7 | 2.4 | 2.3 | 0.0 | 3.9 | 39.3 | 54.5 |
| 12 | 30/70 | 0.095 | 64.5 | 33.3 | 2.2 | 2.6 | 13.2 | 5.5 | 40.0 | 38.7 |
| 13 | 70/30 | 0.053 | 78.3 | 19.5 | 2.2 | 4.4 | 31.2 | 7.6 | 40.1 | 16.7 |

EXAMPLE 14-16

Extraction of Hexane with Methanol Aqueous Solution

Example 6 is repeated except hexane, instead of decane, is used and the extracting solutions are water, 30/70, and 70/30 methanol/water solutions, respectively, in Examples 14, 15, and 16. The results are listed in Table 4.

EXAMPLE 17-19

Extraction of Octane with Methanol Aqueous Solution

Example 6 is repeated except octane, instead of decane, is used and the extracting solutions are water, 30/70, and 70/30 methanol/water solutions, respectively, in Examples 17, 18, and 19. The results are listed in Table 5.

TABLE 4

Extraction of Hexane with Methanol Aqueous Solution

| Ex. No. | MeOH/H$_2$O (V/V) extracting solution | Organic/ aqueous (W/W) | Organic phase composition, wt % | | | Aqueous phase composition, wt % | | | | |
|---|---|---|---|---|---|---|---|---|---|---|
| | | | Hexane | MeI | AcOH | Hexane | MeOH | MeI | AcOH | H$_2$O |
| 14 | 0/100 | 0.113 | 55.9 | 41.7 | 2.4 | 1.5 | 0 | 3.5 | 39.8 | 55.2 |
| 15 | 30/70 | 0.110 | 64.5 | 33.3 | 2.2 | 2.0 | 13.3 | 5.0 | 40.5 | 39.2 |
| 16 | 70/30 | 0.068 | 78.3 | 19.5 | 2.2 | 3.6 | 31.6 | 7.3 | 40.6 | 16.9 |

TABLE 5

Extraction of Octane with Methanol Aqueous Solution

| Ex. No. | MeOH/H$_2$O (V/V) extracting solution | Organic/ aqueous (W/W) | Organic phase composition, wt % | | | Aqueous phase composition, wt % | | | | |
|---|---|---|---|---|---|---|---|---|---|---|
| | | | Octane | MeI | AcOH | Octane | MeOH | MeI | AcOH | H$_2$O |
| 17 | 0/100 | 0.133 | 57.0 | 41.4 | 1.9 | 0.8 | 0.0 | 3.1 | 40.1 | 56.0 |
| 18 | 30/70 | 0.116 | 62.8 | 35.5 | 1.6 | 1.0 | 13.6 | 4.5 | 40.9 | 40.0 |
| 19 | 70/30 | 0.104 | 76.0 | 22.1 | 1.9 | 1.6 | 32.5 | 6.9 | 41.8 | 17.2 |

EXAMPLE 20-22

Extraction of 2,2-dimethylbutane with Acetic Acid Aqueous Solution

Example 1 is repeated except 2,2-dimethylbutane (DMB), instead of decane, is used and the extracting solutions are water, 30/70, and 70/30 acetic acid/water solutions, respectively, in Examples 20, 21, and 22. The results are listed in Table 6.

TABLE 6

Extraction of DMB with Acetic Acid Aqueous Solution

| Ex. No. | AcOH/H$_2$O (V/V) extracting solution | Organic/ aqueous (W/W) | Organic phase composition, wt % | | | Aqueous phase composition, wt % | | | |
|---|---|---|---|---|---|---|---|---|---|
| | | | DMB | MeI | AcOH | DMB | MeI | AcOH | H$_2$O |
| 20 | 0/100 | 0.110 | 55.9 | 41.7 | 2.4 | 2.3 | 3.9 | 39.2 | 54.6 |
| 21 | 30/70 | 0.100 | 61.0 | 34.7 | 4.3 | 2.5 | 5.0 | 55.0 | 37.5 |
| 22 | 70/30 | 0.073 | 66.6 | 22.2 | 11.2 | 3.6 | 6.6 | 74.4 | 15.4 |

EXAMPLE 23-25

Extraction of Hexane with Acetic Acid Aqueous Solution

Example 1 is repeated except hexane, instead of decane, is used and the extracting solutions are water, 30/70, and 70/30 acetic acid/water solutions, respectively, in Examples 23, 24, and 25. The results are listed in Table 7.

TABLE 7

Extraction of Hexane with Acetic Acid Aqueous Solution

| Ex. No. | AcOH/H$_2$O (V/V) extracting solution | Organic/ aqueous (W/W) | Organic phase composition, wt % | | | Aqueous phase composition, wt % | | | |
|---|---|---|---|---|---|---|---|---|---|
| | | | Hexane | MeI | AcOH | Hexane | MeI | AcOH | H$_2$O |
| 23 | 0/100 | 0.113 | 57.3 | 40.7 | 2.0 | 1.5 | 3.5 | 39.8 | 55.2 |
| 24 | 30/70 | 0.116 | 61.0 | 34.9 | 4.1 | 1.7 | 4.6 | 55.8 | 37.9 |
| 25 | 70/30 | 0.087 | 66.4 | 23.6 | 10 | 2.9 | 6.3 | 75.3 | 15.7 |

EXAMPLE 26-28

Extraction of Octane with Acetic Acid Aqueous Solution

Example 1 is repeated except octane, instead of decane, is used and the extracting solutions are water, 30/70, and 70/30 acetic acid/water solutions, respectively, in Examples 26, 27, and 28. The results are listed in Table 8.

TABLE 8

Extraction of Octane with Acetic Acid Aqueous Solution

| Ex. No. | AcOH/H$_2$O (V/V) extracting solution | Organic/ aqueous (W/W) | Organic phase composition, wt % | | | Aqueous phase composition, wt % | | | |
|---|---|---|---|---|---|---|---|---|---|
| | | | Octane | MeI | AcOH | Octane | MeI | AcOH | H$_2$O |
| 26 | 0/100 | 0.138 | 57.0 | 41.4 | 1.9 | 0.8 | 3.0 | 40.2 | 56.4 |
| 27 | 30/70 | 0.122 | 63.1 | 33.6 | 3.2 | 1.1 | 4.6 | 56.2 | 38.1 |
| 28 | 70/30 | 0.110 | 69.3 | 22.3 | 8.4 | 1.5 | 6.1 | 76.5 | 15.9 |

EXAMPLE 29-33

Extraction of Mixed Alkanes with Acetic Acid Aqueous Solution

Example 1 is repeated but the simulated bottoms stream contains 61.9 wt % of acetic acid, 12.3 wt % of methyl iodide, 6.1 wt % of methyl acetate, 2.3 wt % of 2-methylpentane, 7.2 wt % of 3-methylpentane, 7.3 wt % of C7 or higher alkanes, and 2.9 wt % of other impurities. The simulated bottoms stream is mixed with an acetic acid aqueous solution (acetic acid/water 50:50 in volume) in various ratios as indicated in Table 9. The compositions of the organic phase and the aqueous phase are listed in Table 9.

TABLE 9

Extraction of Alkanes with Acetic Acid Aqueous Solution

| Ex. No. | Extracting solution/ bottom stream (W/W) | Organic/ aqueous (W/W) | Organic phase composition, wt % | | | | | Aqueous phase composition, wt % | | | | | |
|---|---|---|---|---|---|---|---|---|---|---|---|---|---|
| | | | Alkanes | MeI | AcOH | MeOAc | Others | Alkanes | MeI | AcOH | MeOAc | H$_2$O | Others |
| 29 | 1 | 0.151 | 66.2 | 26.3 | 5.0 | 1 | 1.5 | 0.1 | 3.5 | 66.0 | 0.2 | 30.0 | 0.2 |
| 30 | 2 | 0.082 | 69.0 | 25.0 | 3.8 | 0.7 | 1.5 | 0.3 | 2.6 | 59.8 | 0.1 | 37.1 | 0.1 |
| 31 | 4 | 0.047 | 75.8 | 19.2 | 3.1 | 0.4 | 1.5 | <0.1 | 1.8 | 55.7 | <0.1 | 42.4 | <0.1 |
| 32 | 9 | 0.020 | 81.4 | 14.7 | 2.5 | 0.2 | 1.2 | <0..1 | 1.0 | 52.8 | <0.1 | 46.1 | <0.1 |
| 33 | 15 | 0.011 | 83.8 | 13.0 | 2.3 | 0.1 | 0.8 | 0.1 | 0.6 | 51.7 | <0.1 | 47.5 | <0.1 |

We claim:

1. A method for removing a hydrocarbon impurity from an acetic acid production process, said method comprising:
   (a) reacting methanol and carbon monoxide in the presence of a carbonylation catalyst, a catalyst stabilizer, methyl iodide, water and methyl acetate to produce an acetic acid stream containing a hydrocarbon impurity;
   (b) flashing at least a portion of the acetic acid stream into a vapor stream comprising acetic acid, water, methanol, methyl acetate, methyl iodide and the hydrocarbon impurity, and a liquid stream comprising the catalyst and the catalyst stabilizer;
   (c) separating the vapor stream from step (b) by distillation into a product stream comprising acetic acid and a minor amount of water, and an overhead stream comprising methyl iodide, water, methyl acetate, acetic acid and the hydrocarbon impurity;
   (d) condensing and separating the overhead stream from step (c) into a light, aqueous phase comprising water, acetic acid, and methyl acetate, and a heavy, organic phase comprising methyl iodide, acetic acid, methyl acetate, and the hydrocarbon impurity; and
   (e) distilling at least a portion of the heavy, organic phase from step (d) into a vapor stream comprising the majority of methyl iodide and a bottoms stream comprising the majority of acetic acid, methyl acetate, methyl iodide, and the hydrocarbon impurity;
   (f) extracting the bottoms stream from step (e) with water, an acetic acid aqueous solution, or with a methanol aqueous solution, and forming an organic phase comprising the majority of the hydrocarbon impurity and an aqueous phase comprising the majority of water, acetic acid, methyl iodide, and optional methanol; and
   (g) recycling the aqueous phase from step (f) to the carbonylation reaction of step (a).

2. The method of claim 1, wherein the catalyst is a rhodium catalyst.

3. The method of claim 1, wherein the catalyst stabilizer is triphenylphosphine oxide.

4. The method of claim 1, wherein the concentration of water in step (a) is within the range of about 2 wt % to about 10 wt % of the reaction mixture.

5. The method of claim 1, wherein the hydrocarbon impurity is selected from the group consisting of alkanes, alkenes, aromatics, and mixtures thereof.

6. The method of claim 1, wherein the heavy, organic phase of step (d) comprises from about 60 wt % to about 90 wt % of methyl iodide, about 1 wt % to about 10 wt % of acetic acid, about 2 wt % to about 15 wt % of methyl acetate, about 1 wt % to about 10 wt % of the hydrocarbon impurity, and about 0.01 wt % to about 1 wt % of water.

7. The method of claim 1, the distillation of step (e) is conducted at an overhead temperature less than 75° C.

8. The method of claim 1, wherein the distillation of step (e) is conducted at an overhead temperature within the range of about 43° C. to about 75° C.

9. The method of claim 1, wherein the distillation of step (e) is conducted at an overhead temperature within the range of about 43° C. to about 60° C.

10. The method of claim 1, wherein the distillation of step (e) is conducted at an overhead temperature within the range of about 43° C. to about 45° C.

11. A method for separating methyl iodide and hydrocarbon, said method comprising extracting a mixture comprising methyl iodide and a hydrocarbon with an extracting solution selected from the group consisting of water, acetic acid aqueous solutions, and ethanol aqueous solutions, and forming an organic phase comprising the hydrocarbon and an aqueous phase comprising methyl iodide, wherein the hydrocarbon is selected from the group consisting of alkanes, alkene, aromatics, and mixtures thereof.

12. The method of claim 11, wherein the hydrocarbon is a C3-C12 alkane or a mixture thereof.

13. The method of claim 11, wherein the extracting solution is an acetic acid aqueous solution.

14. The method of claim 11, wherein the extracting solution is a methanol aqueous solution.

15. The method of claim 11, wherein the aqueous phase is introduced to a methanol carbonylation reaction.

* * * * *